United States Patent [19]

Nilsson et al.

[11] Patent Number: 5,726,183

[45] Date of Patent: Mar. 10, 1998

[54] NEW USE OF QUINOLINE-3-CARBOXAMIDE COMPOUNDS

[75] Inventors: Bo Nilsson, Helsingborg; Agneta Svedberg; Per Gjörstrup, both of Lund, all of Sweden

[73] Assignee: Pharmcia & Upjohn, Stockholm, Sweden

[21] Appl. No.: 704,587

[22] PCT Filed: Mar. 8, 1995

[86] PCT No.: PCT/SE95/00245

§ 371 Date: Oct. 29, 1996

§ 102(e) Date: Oct. 29, 1996

[87] PCT Pub. No.: WO95/24196

PCT Pub. Date: Sep. 14, 1995

[30] Foreign Application Priority Data

Mar. 10, 1994 [SE] Sweden .................................. 9400810

[51] Int. Cl.[6] ...................................................... A61K 31/47
[52] U.S. Cl. ............................................. 514/312; 514/311
[58] Field of Search ..................................... 514/312, 311

[56] References Cited

U.S. PATENT DOCUMENTS

| | | | |
|---|---|---|---|
| 3,960,868 | 6/1976 | Ferrini et al. | 260/287 |
| 4,107,310 | 8/1978 | Allais et al. | 424/258 |
| 4,547,511 | 10/1985 | Eriksoo et al. | 514/312 |
| 4,738,971 | 4/1988 | Eriksoo et al. | 514/312 |
| 5,310,913 | 5/1994 | Gunnarsson et al. | 546/155 |

FOREIGN PATENT DOCUMENTS

| | | |
|---|---|---|
| 4323948 | 10/1968 | Japan . |
| 9015052 | 12/1990 | Japan . |
| 9112804 | 5/1991 | Japan . |
| 9114432 | 10/1991 | Japan . |
| 9204325 | 3/1992 | Japan . |
| 9207833 | 5/1992 | Japan . |
| 9216104 | 10/1992 | Japan . |
| 9306829 | 4/1993 | Japan . |

OTHER PUBLICATIONS

Carlsten, H., et al., *APMIS*, 97:728–732, 1989.
Cook, S.D., et al., *Ann. Neurol.*, 22:634–638, 1987.
Coppola, G. M., et al., *Organic Mag. Res.*, 17(9): 242–245, 1981.
Dhib–Jalbut, S., et al., *Annal. Allergy*, 64:433–444, 1990.
Fabian, W.M.F., et al., *J. Med. Structure*, 317:1–15, 1994.
Hauser, S.L., *N. Eng. J. Med.*, 308:173–183, 1983.
Hirozumi, I., *Chem. Abstracts*, 116(23):85, 1992.
Kalland, T., et al., *J. Immunol.*, 134:3956–3961, 1985.
Kalland, T., *Cancer Res.*, 46:3018–3022, 1986.
Kalland, T., *J. Immunol.*, 144:4472–6, 1990.
Kappos, L., *Ann. Neurol.*, 23:56–63, 1988.
Karussis, D.M., *Autoimmunity*, 1992:101.
Karussis, D.M., *J. Neurol.*, 1992, 239 (suppl 2):S96.
Karussis, D.M., *Neurology*, 42 (suppl 3):346, 1992.
Karussis, D.M., *J. Neuroimmunol.*, 1991; 1 (suppl):159.

Larsson, E.L., et al., *Int. J. Immunopharmacol.*, 9:425–431, 1987.
Mehta, P.J., *Neurol.*, 32:372–77, 1982.
Myrianthopoulos, N.C., *Handbook of Clinical Neurology*, 3(47):289–317, 1985.
Oksenberg, J.R., et al., *Nature*, 345:344–347, 1990.
Patzold, U., et al., *J. Neurolog. Sci.*, 54:377–394, 1982.
Prineas, J.W., Koetsier, J.C. (ed.) *Handbook of Clinical Neurology*, pp. 213–257, Elsevier Science Publ., Amsterdam, 1985.
Shridar, D.R., Sastry, C.V., Mehrotra, A.K., *Indian Journal of Chemistry*, 17B:488–490, 1979.
Tarkowski, A., et al., *Arthr. Rheum.*, 29(11):1405–1409, 1986.
DiPiro et al., *Pharmacotherapy, A Pathophysical Approach*, pp. 961–965, 1989.
Shridar et al., *Indian Journal of Chemistry*, 17B:488–490, 1979.

*Primary Examiner*—Marianne M. Cintins
*Assistant Examiner*—Dwayne C. Jones
*Attorney, Agent, or Firm*—Pravel, Hewitt, Kimball & Krieger

[57] ABSTRACT

A method of treating psoriasis with a quinoline-3-carboxamide compound comprising the structure (I) below, optionally with substituents for the hydrogen atoms shown ($H^{1-9}$), or a pharmaceutically acceptable salt of said compound, where (a) ——— represents that there are two conjugated double bonds between the atoms comprised by the dashed line, (b) $X_1$ and $X_2$ are separately selected from an oxygen atom or an $NH^9$ group, said $X_1$ and $X_2$ being bound by a single bond to the ring when attached to $H^7$ or $H^8$ and by a double bond when not bound to $H^7$ or $H^8$, (c) $H^{1-9}$ are hydrogens with the provision that $H^9$ is only present when at least one of $X_1$ and $X_2$ is the $NH^9$-group, (d) $H^7$ and $H^8$ are hydrogens that are attached to different atoms selected among $X_1$, $X_2$ and the nitrogen atoms (N) in the quinoline ring, for the manufacture of a composition intended for treating psoriasis or conditions associated with psoriasis. Also described are methods for treating psoriasis or conditions associated with psoriasis in which methods the above compounds are administered to a living body. Particularly preferred compounds are N-phenyl-N-methyl-1,2-dihydro-4-hydroxy-1-methyl-2-oxo-quinoline-3-carboxamide or a salt thereof

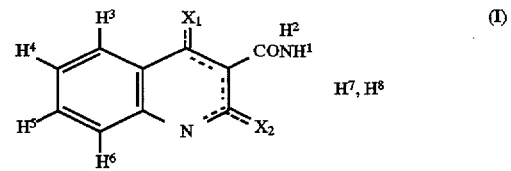

6 Claims, No Drawings

NEW USE OF QUINOLINE-3-CARBOXAMIDE COMPOUNDS

This application is a 371 of PCT/SE95/00245, filed Mar. 8, 1995.

The present invention concerns the use of quinoline-3-carboxamide compounds, in particular roquinimex (Linomide®), or a pharmaceutically acceptable salt thereof for treating psoriasis or conditions associated with psoriasis.

BACKGROUND OF THE INVENTION

Psoriasis is a common disease which affects about 2% of the population of Scandinavia.

Hereditary factors are important. If one parent has psoriasis, the risk for the child is 25% and if both parents have psoriasis there is a risk of 60–70%. Drugs thought to precipitate or worsen psoriasis include alcohol and, in some patients, β-blockers and non-steroidal anti-inflammatory agents.

Psoriasis is characterised by thickened, erythematous, well-demarcated areas of skin covered by silvery scales. The extent of involvement ranges from isolated, small lesions to the whole body surface. Nails are involved in up to 50% of psoriasis patients. Because of the heterogenic nature of psoriasis, other papulosquamous dermatoses may need to be considered in the differential diagnosis. There are several clinical forms of psoriasis and it can change qualitatively from stable plaque lesions to an unstable form typified by eruptive inflammatory lesions.

Psoriatic arthritis is defined as "psoriasis (of skin or nails) associated with inflammatory arthritis (peripheral and/or spinal) and usually a negative serological test for rhematoid factor". The incidence of arthritis in the psoriatic population is about 7%. The clinical features of psoriatic arthritis are: (1) distal arthitis—an asymmetrical arthritis involving the terminalinterphalangeal joints of the hands and interphalangeal joints of the toes; there is invariably nail involvement; (2) artrophathy indistinguishable from rheumatoid arthritis, although milder; (3) a severe deforming type of arthristis (psoriatic arthritis mutilans), producing osteolysis of the hands and feet, usually associated with severe inflammatory forms of psoriasis; (4) an ankylosing spondylopathy; and (5) a mono-arthritis or oligo-arthritis.

Psoriasis is not a static disease: seasonal fluctuations, spontaneous remissions, and physical and emotional weltbeing all affects the disease and hence its management. Most patients with localised, plaque-type psoriasis are able to centroll their disease at home with topical therapy with corticosteroid creams and ointments. For the more widespread forms, some form of phototherapy, either alone or combined with topical therapy, is usually needed. In resistant psoriasis, photochemotherapy or systemic therapy may be indicated.

Methotrexate is indicated only for recalcitrant psoriasis, unresponsive to topical therapy. The main side effects are acute marrow suppression and a long term risk of hepatic fibrosis and cirrhosis which is related to cumulative life time dosage and regimen employed. Retinoid is a generic name that includes naturally occuring compounds with vitamin A activity and any synthetic analogues of retinol. As with methotrexate, retonoid therapy is restricted to severe, recalcitrant psoriasis. It is especially valuable for initial treatment of the severe, inflammatory forms of the disease, that is erythrodermic or postular psoriasis, producing a more rapid response than methotrexate. Cyklosporin is effective for severe psoriasis, and providing that guidelines for treatment are observed it also seems safe when used over periods of up to a year. However, as the long term safety of cyklosporin in patients with psoriasis is still to be established it is not the drug of choice for the patient likely to be require continous treatment for many years. The main side effects are hypertension and renal impairment, both of which are reversible if guidelines for treatment are followed. In other clinical conditions, such as immunesuppression after transplantation, the incidence of lymphoma is increased in people receiving cyklosporin long term.

Quinoline-3-carboxamide compounds have been suggested as pharmaceuticals. The compounds have comprised the structure given in formula I below, optionally with substituents for the hydrogen atoms shown ($H^{1-9}$, where $H^9$ is part of $X_1$ or $X_2$ as shown in (b) below) and, where appropriate, salts of the compounds.

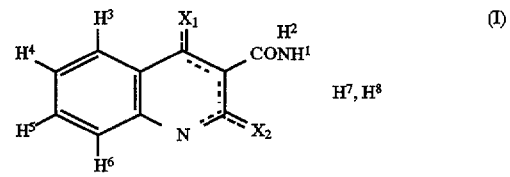

(I)

This formula is a collective formula for the tautomeric structures II–IV.

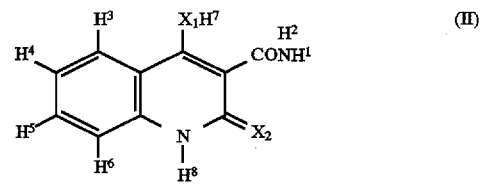

(II)

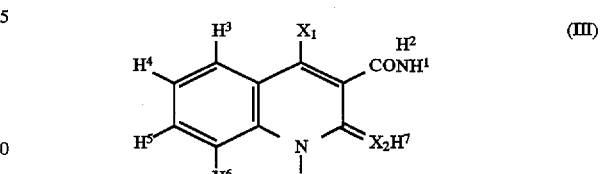

(III)

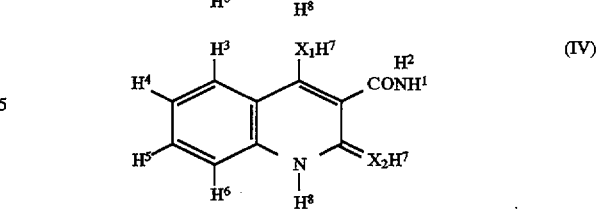

(IV)

In formula I–IV:

(a) ——— represents that there are two conjugated double bonds between the atoms comprised by the dashed line (only formula I).

(b) $X_{1\ and\ X2}$ are separately selected from an oxygen atom or an $NH^9$ group that possibly is substituted, said $X_1$ and $X_2$ being bound by a single bond to the ring when attached to $H^7$ or $H^8$ and by a double bond when not bound to $H^7$ or $H^8$.

(c) $H^{1-9}$ are hydrogens, with the provision that $H^9$ is only present when at least one of $X_1$ and $X_2$ is the $NH^9$ group.

(d) $H^7$ and $H^8$ are hydrogens that are attached to different atoms selected among $X_1$, $X_2$ and the nitrogen atom in the quinoline ring said $X_1$ and $X_2$ being bound by a single bond to the ring when attached to $H^7$ or $H^8$ and by a double bond when not bound to $H^7$ or $H^8$.

The substituents that are to replace $H^{1-9}$ may, according to the prior art, comprise any substituent that gives compounds that can be isolated. See for instance Indian Journal of Chemistry Vol 17B (1979) 488–90 (anti-inflammatory properties), U.S. Pat. No. 3,960,868 (=GB 1,467,061, analgesic, anti-conceptive, anti-inflammatory and anti-allergic properties), U.S. Pat. Nos. 4,547,511 and 4,738,971 (enhancing cell-mediated immunity), WO 9015052 (=U.S. Ser. No. 651,234, filed May 31, 1990) (immunemodulator), U.S. Pat. No. 4,107,310 (analgetics) and JP 68023948 (bacteriocides). Patents and patent applications given above are hereby incorporated by reference. In general it can be stated that many of the compounds comprising structure I are classified as immune modulators with individual effects .spanning the spectra from suppression to stimulation of the immune system. The specific effect achieved depends on the substituents.

One of the most important compounds with formula I are the 1,2-dihydro-hydroquinoline-3-carboxamides, particularly N-phenyl-N-methyl-1,2-dihydro-4-hydroxy-1-methyl-2-oxo-quinoline-3-carboxamide (roquinimex, trade mark Linomide®), i.e. structures I and II with a substituent for $H^1$ that equals phenyl, for $H^2$ that equals methyl, for $H^8$ that equals methyl (attached to the nitrogen atom of the quinoline ring), with no substituents for $H^{3-7}$, with $H^7$ attached to $X_1$, and with each of $X_1$ and $X_2$ equaling an oxygen atom. The compound has double bonds between positions 3 and 4 and between position 2 and $X_2$.

The scientific experimentation with roquinimex has shown that roquinimex has multiple immunological activities. It has thus been found that roquinimex increases the proliferative response to T and B cell mitogens [28], enhances antibody production [29] and augments NK cell activity [30, 31]. Moreover, its immunostimulating and immunoregulating properties may be useful in the treatment of tumors [32] and systemic lupus erythematosis [33, 34] as suggested in U.S. Pat. Nos. 4,547,511 and 4,738,971.

Published PCT-application WO 91/12804 discloses roquinimex as a drug for the treatment of retrovirus infections. WO 91/14432 discloses roquinimex as a drug for regenerating lymphoid cells in patients treated with autologous bone marrow transplantation. WO 93/06829 discloses roquinimex as a drug for the treatment of multiple sclerosis. These published patent applications am hereby incorporated by reference.

Quinoline-3-carboxamide compounds according to the present invention are hitherto not known for treating psoriasis. JP 4041425 (TANABE SEIYAKU CO) discloses 5-Lipoxygenase inhibitors containing 4-aminophenol derivatives or salts thereof which are claimed as remedies for i.a. psoriasis. One such derivative is the amide of the 4-aminophenol derivative of 3-quinoline carboxylic acid. This 3-quinoline carboxylic acid moiety anyhow completely lacks the characteristic substitution pattern which is essential for the compounds of the present invention.

SUMMARY OF THE INVENTION

According to the present invention it has now surprisingly been shown that treatment with quinoline-3-carboxamide compounds, in particular roquinimex (Linomide®), or a pharmaceutically acceptable salt thereof for treating psoriasis or conditions associated with psoriasis.

Cyklosporin A which is a potent immune suppressor interfering with T cell reponse has shown to be effective in treating severe psoriasis. Roquinimex completely abolishes the immunosupressive effect of Cyklosporin in a heart allograft model.

Roquinimex may be used as such or as a pharmaceutically acceptable salt thereof. Furthermore, roquinimex can be used in combination with other agents. Formulations that could be used according to the present invention are disclosed in U.S. Pat. No. 4,547,511 col. 11.

OBJECTIVES OF THE INVENTION

One major objective of the invention is to provide a method for treating psoriasis or conditions associated with psoriasis with quinoline-3-carboxamide compounds, in particular roquinimex (Linomide®), or a pharmacologically acceptable salt thereof.

Further objectives are to provide drugs to be used for the manufacture of pharmaceutical compositions for the treatment of the conditions given in the preceding sentence.

Other objectives of the invention will become apparent to one skilled in the art, and still other objectives will become apparent hereinafter.

Patient studies

Two patients with psoriasis have so far been subjected to long term treatement with roquinimex. The patients had advanced renal cell carcinoma and were treated with roquinimex in a phase II-study (CTN: T89OL01) with a dose of 15 mg twice weekly.

EXAMPLE 1

Patient No.10: His psoriasis engaged knees, capitillum, nails, eye lashes, hands and elbows. After six months of treatment with roquinimex he was completely recovered from his psoriasis. The patient was treated for a total of seventeen months. He received a partial remission of his renal cell carcinoma after seven months of treatment with a response duration of fifteen months. Six months after treatment withdrawal his psoriasis reappeared, although to lesser extent than before.

EXAMPLE 2

Patient No. 15: His psoriasis improved during treatment with roquinimex and he was completely recovered after seventeen months. His renal cancer stabilized during treatment and the treatment was terminated after two years due to progressive disease.

None of the patients had any other concomitant therapy for their psoriasis.

What is claimed is:

1. A method for treating a patient suffering from, or at risk of acquiring, psoriasis or conditions associated with psoriasis, comprising administering to the patient an effective therapeutic dose of N-phenyl-N-methyl-1,2-dihydro-4-hydroxy-1-methyl-2-oxo-quinoline-3-carboxamide or tautomers thereof, or a pharmaceutically acceptable salt thereof.

2. The method of claim 1, wherein the compound is administered orally.

3. The method of claim 1, whereby said compound is administered by injection.

4. The method of claim 1, whereby said compound is administered parenterally.

5. The method of claim 1, 2, 3, or 4, wherein the effective amount is from about 0.01 to about 10 mg/kg body weight and the amount is administered from once daily to once every two weeks.

6. The method of claim 5, wherein the effective amount is from about 0.05 to about 1 mg/kg body weight.

* * * * *